United States Patent
Greaves et al.

(10) Patent No.: US 10,945,963 B2
(45) Date of Patent: Mar. 16, 2021

(54) PHOTOSENSITIVE CAPSULES AND COSMETIC AND PHARMACEUTICAL USE THEREOF

(71) Applicant: L'OREAL, Paris (FR)

(72) Inventors: Andrew Greaves, Magny-le-Hongre (FR); Gleb Sukhorukov, London (GB); Qiangying Yi, London (GB)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/025,098

(22) PCT Filed: Sep. 27, 2014

(86) PCT No.: PCT/EP2014/070130
§ 371 (c)(1),
(2) Date: Mar. 25, 2016

(87) PCT Pub. No.: WO2015/044084
PCT Pub. Date: Apr. 2, 2015

(65) Prior Publication Data
US 2016/0235685 A1   Aug. 18, 2016

(30) Foreign Application Priority Data

Sep. 27, 2013 (FR) ...................... 1359320

(51) Int. Cl.
| | |
|---|---|
| *A61K 9/50* | (2006.01) |
| *A61K 8/11* | (2006.01) |
| *A61Q 19/02* | (2006.01) |
| *A61K 8/84* | (2006.01) |
| *A61K 8/81* | (2006.01) |

(52) U.S. Cl.
CPC .............. *A61K 9/5031* (2013.01); *A61K 8/11* (2013.01); *A61K 8/8194* (2013.01); *A61K 8/84* (2013.01); *A61K 9/5073* (2013.01); *A61Q 19/02* (2013.01); *A61K 2800/81* (2013.01)

(58) Field of Classification Search
CPC .. A61K 9/5031; A61K 9/5073; A61K 8/8194; A61K 8/84; A61K 8/11; A61K 2800/81; A61Q 19/02
See application file for complete search history.

(56) References Cited

U.S. PATENT DOCUMENTS

2007/0072775 A1\* 3/2007 van Boxtel-Verhoeven ................ A01N 25/12
504/367
2008/0020051 A1\* 1/2008 Dahne .................. A61K 9/5073
424/490

OTHER PUBLICATIONS

Zhang, Photoswitched Protein Adsorp. SA Azobenzene Films, CHEMPHYSCHEM, 2012, p. 2671).\*

\* cited by examiner

*Primary Examiner* — David J Blanchard
*Assistant Examiner* — Thurman Wheeler
(74) *Attorney, Agent, or Firm* — Polsinelli PC (57) ABSTRACT

The invention relates to capsules of core/shell type, the core comprising an active agent; the shell comprising one or more concentric and alternating layers of a first photosensitive anionic amino polymer and of a second cationic polymer. The invention also relates to a cosmetic or pharmaceutical composition comprising such capsules. The invention also relates to a non-therapeutic cosmetic process for treating keratin materials, comprising the application to the keratin materials of a cosmetic composition comprising the said capsules, followed by exposure of the deposit formed on the keratin materials to natural light or to artificial light with a wavelength of between 360 and 600 nm.

19 Claims, 1 Drawing Sheet spectral ilrradiance (W.m⁻².nm⁻¹) depending on the wavelength (nm)

Figure 1

Calibration curve of adenosine in artificial sweat

Figure 2

PHOTOSENSITIVE CAPSULES AND COSMETIC AND PHARMACEUTICAL USE THEREOF

CROSS REFERENCE TO RELATED APPLICATIONS

This application is a National Phase filing under 35 U.S.C. § 371 of PCT/EP2014/070130 filed on Sep. 22, 2014; and this application claims priority to Application No. 1359320 filed in France on Sep. 75, 2013 under 35 U.S.C. § 119. The entire contents of each application are hereby incorporated by reference.

The present invention relates to photosensitive capsules for the controlled release of active agents, and also to the cosmetic and pharmaceutical uses thereof.

Active agents such as cosmetic active agents and fragrancing substances are commonly used in cosmetic products. These active agents are generally expensive or volatile or physicochemically unstable or efficient over excessively short periods. There is thus a need to optimize the amount thereof in order to limit the costs, to improve their stability, to protect them from their environment in order especially to prevent their degradation, or alternatively to improve their efficacy over time.

Hollow polymer particles containing cosmetic or pharmaceutical active agents or fragrances are known from document U.S. Pat. No. 6,616,946. The permeability of these particles changes in response to an environmental change such as the pH, the temperature, light, the ionic strength, the electric field, the magnetic field or the solvent. However, such particles do not always show good leaktightness especially during the storage of the composition over time, and the encapsulated active agent escapes from the capsules.

There is thus a need for photosensitive capsules that allow leaktight encapsulation of the active agent. There is also a need for capsules that afford efficient release of the active agent after application of the capsules to keratin materials and exposure to light.

The Applicant has discovered that these needs are satisfied by preparing capsules whose shell comprises one or more alternating layers of a first particular photosensitive anionic polymer and of a second cationic polymer as defined below.

Such capsules have the advantage of having good leaktightness properties, especially during their storage in a cosmetic or pharmaceutical composition.

They also make it possible, after application to keratin materials and exposure to light, to produce release of the encapsulated active agent over a long period, especially of at least 1 day, or even from 1 to 5 days.

Thus, one subject of the present invention is capsules of core/shell type, the core comprising an active agent; the shell comprising one or more concentric and alternating layers of a first photosensitive anionic polymer and of a second cationic polymer as described below.

A subject of the invention is also a cosmetic or pharmaceutical composition comprising, in a physiologically acceptable medium, the capsules as described previously.

A subject of the invention is also a non-therapeutic cosmetic process for treating keratin materials, comprising the application to the keratin materials of a cosmetic composition as described previously, followed by exposure of the deposit formed on the keratin materials to natural light or to artificial light with a wavelength of between 360 and 600 nm.

The capsules according to the invention, after application to keratin materials and exposure to light (natural light, sunlight or artificial light), gradually release the encapsulated active agent over time.

The capsules also show good leaktightness before their exposure to light: they thus allow good storage of the active agent in the cosmetic or pharmaceutical composition medium before being applied to the keratin materials.

The capsules according to the invention comprise a core containing an active agent and a shell surrounding the core, formed from one or more layers, especially concentric layers, of a first photosensitive anionic polymer and of a second cationic polymer. The shell of the capsules thus has an alternating multilayer structure formed from the said first polymer and the said second polymer. This multilayer structure is thus composed of an alternation of a first layer of the said first polymer and of a second layer of the said second polymer.

Thus, the shell of the capsules consists of layers of first and second polymers of opposite charges: the interaction between the first and second polymers gives the shell good leaktightness. The capsules thus have good leaktightness. When the capsules are deposited on keratin materials and then irradiated with natural or artificial light, the first photosensitive polymer changes conformation, modifying the leaktightness of the shell and giving rise to leakage of the active agent from the capsule. The active agent is then gradually released, over time. The capsules thus allow release of the active agent over a long period, especially ranging from 1 minute to 5 days.

The first polymer present in the shell of the capsules is a photosensitive anionic polymer. The term "photosensitive polymer" means a polymer which changes conformation when it is irradiated with a light radiation.

The first polymer is chosen from amino polymers bearing primary amine groups substituted at a degree of substitution of at least 50% (numerical degree), with a group of formula (Ia) below:

in which:

R and R' denote, independently, a hydrogen atom or a $C_1$-$C_4$ alkyl group or a $C_1$-$C_4$ alkoxy group, or a chlorine or fluorine atom or a nitro group;

R and R' may together form a $C_6$ aromatic ring;

Y denotes a —COOH or —SO3H group, or salts thereof.

Preferably, Y denotes an —$SO_3H$ group.

Preferably, Y denotes a —COOH group.

Preferably, R and R' denote a hydrogen atom.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

Preferably, the salts are chosen from the sodium, potassium, magnesium, strontium, copper, manganese and zinc salts. The sodium salt is preferentially used.

The substituted amino polymer may be chosen from polyallylamines, silicone polymers bearing amine groups such as amodimethicones, trimethylsilyl amodimethicones, poly(lysine)s, 2-($C_1$-$C_4$ aminoalkyl)(meth)acrylate polymers, in particular 2-(aminoethyl)(meth)acrylate polymers, chitosans, etc., it being understood that the primary amine groups of these polymers are substituted as defined previously.

Preferably, the substituted amino polymer is a substituted polyallylamine.

The degree of substitution (by number) of the primary amine groups of the first polymer with the groups (Ia) is greater than 60%, preferably greater than 70%, preferentially greater than 80% and more preferentially greater than 90%.

Advantageously, the first polymer has a weight-average molecular weight ranging from 2000 to 400 000 g/mol.

Poly{1-[4-(3-carboxy-4-hydroxyphenylazo)benzenesulfonamido]-1,2-ethanediyl, sodium salt}, also known as PAZO, is preferably used. Such a polymer corresponds to the following formula:

The first polymer may be prepared in three steps as described below. For simplicity, the initial amino polymer (I) is represented in the form polymer-$NH_2$, it being understood that a single $NH_2$ group of the polymer is indicated to explain the chemical reactions performed to prepare the first polymer. These reactions are performed on at least 50% by number of the primary amine groups of the starting polymer.

Step 1

Step 2

Step 3

-continued

[VI]

Step 1:

The polymer bearing primary amine groups (I) is reacted with a halosulfonyl compound (II) in which X=Cl or Br, R and R' being as defined previously, in the presence of an alkaline agent such as sodium hydroxide or calcium carbonate, in a protic or aprotic solvent such as water, tetrahydrofuran or acetonitrile, at a temperature between 0° C. and 150° C. This condensation reaction is known to those skilled in the art. Reference may be made to March's book *Advanced Organic Chemistry: Reactions, Mechanisms, and Structure* ISBN 0-47158589-0, page 1440 paragraph 16-79 "Formation of Acyl Halides from Carboxylic Acids", and to the article by Pizey, J. S. *Synthetic Reagents,* Vol. 1, Wiley, N.Y., 1974, pp. 321-357.

As examples of compounds (II), use may be made of the following compounds:

| Registry number | | |
|---|---|---|
| 121-60-8 | n-acetylsulfanilyl chloride |  |
| 349-71-3 | 4-(acetylamino)-3-fluorobenzene-sulfonyl chloride |  |
| 16761-18-5 | 4-acetamido-3-chlorobenzene-sulfonyl chloride |  |

-continued

| Registry number | | |
|---|---|---|
| 5690-20-0 | 4-(acetylamino) naphthalene-1-sulfonyl chloride |  |

Compounds [II] may be synthesized by acetylation of compounds [VII] followed by halogenation of compounds [VIII] using thionyl chloride or bromide (SOX2 with X=Cl or Br) according to the following synthetic scheme:

These reactions are known to those skilled in the art. Reference may be made to March's book *Advanced Organic Chemistry: Reactions, Mechanisms and Structure* ISBN 0-47158589-0.

As examples of compounds [VII], mention may be made of the following compounds:

| Registry number | | |
|---|---|---|
| 6387-14-0 | 4-amino-5-chloro-m-toluenesulfonic acid |  |
| 98-33-9 | 2-aminotoluene-5-sulfonic acid |  |
| 133-78-8 | m-toluidine-4-sulfonic acid |  |

| Registry number | | |
|---|---|---|
| 6471-78-9 | 4-amino-5-methoxy-2-methylbenzene-sulfonic acid | |
| 616-84-2 | 2-nitroaniline-4-sulfonic acid | |
| 712-24-3 | 3-nitroaniline-4-sulfonic acid | |
| 88-50-6 | 2,5-dichlorosulfanilic acid | |

Step 2:

This step consists in performing the deprotection of the amine group. The amide (III) is hydrolysed under conditions known to those skilled in the art, for example hydrolysis at alkaline pH in the presence of a base such as sodium hydroxide. Reference may be made to March's book *Advanced Organic Chemistry: Reactions, Mechanisms, and Structure* ISBN 0-47158589-0; Chapter 16, pages 1408-1410.

Step 3:

This step consists in first performing a diazotization reaction on compound (IV) followed by a coupling reaction with an aromatic compound (V). The diazotization reaction takes place in water or a water/ethanol mixture in the presence of sodium nitrite at acidic pH and at a temperature between 0 and 5° C. The reaction takes place rapidly between 1 minute and 2 hours. Coupling with the formed "diazonium" intermediate takes place by pouring this reaction mixture into a solution containing the aromatic compound (V). The solvent may be water, ethanol or a mixture thereof. The pH is controlled to ensure that the coupling reaction takes place. This coupling reaction is known: reference may be made to the books *Diazo Chemistry—Synthesis and Reactions,* John Cannell Cain, ISBN 1933998210; *Diazo Chemistry I: Aromatic and Heteroaromatic Compounds,* H Zollinger, ISBN 9783527292134.

As examples of compounds [V], mention may be made of the following compounds:

| Registry number | | |
|---|---|---|
| 69-72-7 | salicylic acid | |
| 877-22-5 | 2-hydroxy-3-methoxybenzoic acid | |
| 303-38-8 | 2,3-dihydroxybenzoic acid | |
| 20244-86-4 | 3-methylsalicylic acid | |
| 5106-98-9 | 4-chlorosalicylic acid | |
| 2237-36-7 | 4-methoxysalicylic acid | |
| 89-86-1 | 2,4-dihydroxybenzoic acid | |
| 50-85-1 | 4-methylsalicylic acid | |
| 303-07-1 | 2,6-dihydroxybenzoic acid | |
| 1829-32-9 | 3-chlorosalicylic acid | |

| Registry number | | |
|---|---|---|
| 5653-46-3 | 2-hydroxy-3,4-dimethoxybenzoic acid |  |
| 10435-55-9 | 4-ethoxy-2-hydroxybenzoic acid |  |
| 50-86-2 | 2-hydroxy-4-acetylaminobenzoic acid |  |
| 548-51-6 | 2-hydroxy-3-isopropyl-6-methylbenzoic acid |  |
| 67531-86-6 | 2-fluoro-6-hydroxybenzoic acid |  |
| 7053-88-5 | 2-hydroxy-3-isopropylbenzoic acid |  |
| 1300-51-2 | sodium 2-hydroxybenzenesulfonate |  |
| 832-49-5 | 1-naphthol-2-sulfonic acid, potassium salt |  |

The second polymer present in the shell of the capsules is a cationic polymer, different from the said first polymer.

The term "cationic polymer" is intended to mean any polymer comprising cationic groups and/or groups that can be ionized to cationic groups. Preferably, the cationic polymer is hydrophilic or amphiphilic. The cationic polymers may be chosen from all those already known per se, i.e. especially those described in documents EP 337 354, FR 2 270 846, FR 2 383 660, FR 2 598 611, FR 2 470 596 and FR 2 519 863.

The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may more particularly be made of polymers of the polyamine, polyaminoamide and polyquaternary ammonium type, such as those described in FR 2 505 348 and FR 2 542 997.

Mention may be made in particular of:

(1) homopolymers or copolymers derived from acrylic or methacrylic esters or amides and comprising at least one of the units of the following formulae:

in which:
- $R_3$, which may be identical or different, denote a hydrogen atom or a $CH_3$ radical;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- $R_4$, $R_5$ and $R_6$, which may be identical or different, represent an alkyl group containing from 1 to 18 carbon atoms or a benzyl radical, preferably an alkyl group containing from 1 to 6 carbon atoms;
- $R_1$ and $R_2$, which may be identical or different, represent a hydrogen atom or an alkyl group containing from 1 to 6 carbon atoms, preferably methyl or ethyl;
- X denotes an anion derived from a mineral or organic acid, such as a methosulfate anion or a halide such as chloride or bromide.

The copolymers of family (1) may also contain one or more units derived from comonomers that may be selected from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), mention may be made of:

- copolymers of acrylamide and of dimethylaminoethyl methacrylate quaternized with dimethyl sulfate or with a dimethyl halide, such as the product sold under the name Hercofloc by the company Hercules,
- copolymers of acrylamide and of methacryloyloxyethyltrimethylammonium chloride, such as those described in EP 080 976 and those sold under the name Bina Quat P 100 by the company Ciba Geigy,
- copolymer of acrylamide and of methacryloyloxyethyltrimethylammonium methosulfate, such as that sold under the name Reten by Hercules,
- quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573,
- dimethylaminoethyl methacrylate/vinylcaprolactam/vinylpyrrolidone terpolymers, such as the product sold under the name Gaffix VC 713 by the company ISP,
- vinylpyrrolidone/methacrylamidopropyldimethylamine copolymers, such as those sold under the name Styleze CC 10 by ISP;
- quaternized vinylpyrrolidone/dimethylaminopropylmethacrylamide copolymers such as the product sold under the name Gafquat HS 100 by the company ISP,
- preferably crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. A crosslinked acrylamide/methacryloyloxyethyltrimethylammonium chloride copolymer (20/80 by weight) in the form of a dispersion comprising 50% by weight of said copolymer in mineral oil may more particularly be used. This dispersion is sold under the name Salcare® SC 92 by the company Ciba. A crosslinked methacryloyloxyethyltrimethylammonium chloride homopolymer comprising about 50% by weight of the homopolymer in mineral oil or in a liquid ester can also be used. These dispersions are sold under the names Salcare® SC 95 and Salcare® SC 96 by the company Ciba.

(2) Cationic polysaccharides, in particular cationic celluloses and cationic galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR patent 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose having reacted with an epoxide substituted by a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, a chloride). Such products are especially sold under the trade names Jaguar C13 S, Jaguar C 15, Jaguar C 17 or Jaguar C162 by the company Rhodia.

(3) Polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers. Such polymers are especially described in FR 2 162 025 and FR 2 280 361;

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are especially described in French patents 2 252 840 and 2 368 508;

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are described in particular in FR 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1. Such polymers are especially described in U.S. Pat. No. 3,227,615 and U.S. Pat. No. 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

in which
k and t are equal to 0 or 1, the sum k+t being equal to 1;
$R_{12}$ denotes a hydrogen atom or a methyl radical;
$R_{10}$ and $R_{11}$, independently of each other, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidinyl or morpholinyl; $R_{10}$ and $R_{11}$, independently of each other, preferably denote an alkyl group containing from 1 to 4 carbon atoms;
$Y^-$ is an anion such as bromide, chloride, acetate, borate, citrate, tartrate, bisulfate, bisulfite, sulfate or phosphate.

These polymers are especially described in FR 2 080 759 and FR 2 190 406. Mention may be made more particularly of the dimethyldiallylammonium salt (for example chloride) homopolymer sold, for example, under the name Merquat 100 by the company Nalco (and homologues thereof of low weight-average molar masses) and the copolymers of diallyldimethylammonium salts (for example chloride) and of acrylamide, sold especially under the names Merquat 550 and Merquat 7SPR.

(8) quaternary diammonium polymers comprising repeating units of formula:

in which:
$R_{13}$, $R_{14}$, $R_{15}$ and $R_{16}$, which may be identical or different, represent aliphatic, alicyclic or arylaliphatic radicals comprising from 1 to 20 carbon atoms, or lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second non-nitrogen heteroatom, or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group in which $R_{17}$ is an alkylene and D is a quaternary ammonium group;

A1 and B1 represent divalent polymethylene groups comprising from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $(CH_2)_n$—CO-D-OC—$(CH_2)_n$— in which D denotes:

a) a glycol residue of formula —O—Z—O—, in which Z denotes a linear or branched hydrocarbon-based radical, or a group corresponding to one of the following formulae: —$(CH_2$—$CH_2$—$O)_x$—$CH_2$—$CH_2$— and —[$CH_2$—$CH(CH_3)$—$O]_y$—$CH_2$—$CH(CH_3)$—, where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—.

Preferably, $X^-$ is an anion such as chloride or bromide.

These polymers have a number-average molar mass (Mn) generally of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Mention may be made more particularly of polymers that are composed of repeating units corresponding to the formula:

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

A particularly preferred compound of formula (IV) is that for which $R_1$, $R_2$, $R_3$ and $R_4$ represent a methyl radical and n=3, p=6 and X=Cl, known as Hexadimethrine chloride according to the INCI (CTFA) nomenclature.

(9) Polyquaternary ammonium polymers comprising units of formula (V):

in which:
- $R_{18}$, $R_{19}$, $R_{20}$ and $R_{21}$, which may be identical or different, represent a hydrogen atom or a methyl, ethyl, propyl, β-hydroxyethyl, β-hydroxypropyl or $CH_2CH_2(OCH_2CH_2)_pOH$ radical, in which p is equal to 0 or to an integer between 1 and 6, with the proviso that $R_{18}$, $R_{19}$, $R_{20}$ and $R_{21}$ do not simultaneously represent a hydrogen atom,
- r and s, which may be identical or different, are integers between 1 and 6,
- q is equal to 0 or to an integer between 1 and 34,
- X— denotes an anion such as a halide,
- A denotes a dihalide radical or preferably represents —$CH_2$—$CH_2$—O—$CH_2$—$CH_2$—.

Such compounds are described especially in patent application EP-A-122 324. Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:
(a) one or more units corresponding to formula (A) below:

(b) optionally one or more units corresponding to formula (B) below:

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis may be performed in an acidic or basic medium.

The weight-average molecular weight of said polymer, measured by light scattering, may range from 1000 to 3 000 000 g/mol, preferably from 10 000 to 1 000 000 and more particularly from 100 000 to 500 000 g/mol.

The cationic charge density of these polymers may range from 2 meq/g to 20 meq/g, preferably from 2.5 to 15 meq/g and more particularly from 3.5 to 10 meq/g.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from those of families (1), (2), (7) and (10) mentioned above.

Among the cationic polymers mentioned above, the ones that may preferably be used are cationic polysaccharides, especially cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, and homologues thereof of low weight-average molecular weights, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

Preferentially, the cationic polymer is chosen from homopolymers or copolymers of dimethyldiallylammonium salts (for example chloride).

More preferentially, the cationic polymer is chosen from homopolymers of dimethyldiallylammonium salts (for example chloride).

The encapsulated active agents may be chosen from fragrancing substances, cosmetic active agents and pharmaceutical active principles.

a) Fragrancing Substances

The term "fragrancing substance" means any perfume or aroma capable of giving off a pleasant odour.

Perfumes are compositions especially containing the starting materials described in S. Arctander, Perfume and Flavor Chemicals (Montclair, N.J., 1969), in S. Arctander, Perfume and Flavor Materials of Natural Origin (Elizabeth, N.J., 1960) and in Flavor and Fragrance Materials—1991, Allured Publishing Co., Wheaton, Ill.

They may also be natural products, for instance essential oils, absolutes, resinoids, resins, concretes, and/or synthetic products (terpene or sesquiterpene hydrocarbons, alcohols, phenols, aldehydes, ketones, ethers, acids, esters, nitriles or peroxides, which may be saturated or unsaturated, and aliphatic or cyclic).

According to the definition given in international standard ISO 9235 and adopted by the Commission of the European Pharmacopoeia, an essential oil is an odoriferous product generally of complex composition, obtained from a botanically defined plant raw material, either by steam entrainment, or by dry distillation, or via an appropriate mechanical process without heating (cold pressing). The essential oil is generally separated from the aqueous phase via a physical process which does not result in any significant change in the composition.

Among the essential oils that may be used according to the invention, mention may be made of those obtained from plants belonging to the following botanical families:

Abietaceae or Pinaceae: conifers; Amaryllidaceae; Anacardaceae; Anonaceae: ylang ylang; Apiaceae (for example Umbelliferae): dill, angelica, coriander, sea fennel, carrot, parsley; Araceae; Aristolochiaceae; Asteraceae: yarrow, artemisia, camomile, helichrysum; Betulaceae; Brassicaceae; Burseraceae: frankincense; Carophyllaceae; Canellaceae; Cesalpiniaceae: copaifera (copaiba balsam); Chenopodaceae; Cistaceae: rock rose; Cyperaceae; Dipterocarpaceae; Ericaceae: gaultheria (wintergreen); Euphorbiaceae; Fabaceae; Geraniaceae: geranium; Guttiferae; Hamamelidaceae; Hernandiaceae; Hypericaceae: St-John's wort; Iridaceae; Juglandaceae; Lamiaceae: thyme, oregano, monarda, savory, basil, marjorams, mints, patchouli, lavenders, sages, catnip, rosemary, hyssop, balm; Lauraceae: ravensara, sweet bay, rosewood, cinnamon, litsea; Liliaceae: garlic; Magnoliaceae: magnolia; Malvaceae; Meliaceae; Monimiaceae; Moraceae: hemp, hop; Myricaceae; Myristicaceae: nutmeg; Myrtaceae: eucalyptus, tea tree, paperbark tree, cajuput, backhousia, clove, myrtle; Oleaceae; Piperaceae: pepper; Pittosporaceae; Poaceae: lemon balm, lemongrass, vetiver; Polygonaceae; Renonculaceae; Rosaceae: roses; Rubiaceae; Rutaceae: all citrus plants; Salicaceae; Santalaceae: sandalwood; Saxifragaceae; Schisandraceae; Styracaceae: benjoin; Thymelaceae: agar wood; Tilliaceae; Valerianaceae: valerian, spikenard; Verbenaceae: lantana, verbena; Violaceae; Zingiberaceae: galangal, turmeric, cardamom, ginger; Zygophyllaceae.

Mention may also be made of the essential oils extracted from flowers (lily, lavender, rose, jasmine, ylang ylang, neroli), from stems and leaves (patchouli, geranium, petitgrain), from fruit (coriander, aniseed, cumin, juniper), from fruit peel (bergamot, lemon, orange), from roots (angelica, celery, cardamom, iris, rattan palm, ginger), from wood (pinewood, sandalwood, gaiac wood, rose of cedar, camphor), from grasses and gramineae (tarragon, rosemary, basil, lemongrass, sage, thyme), from needles and branches (spruce, fir, pine, dwarf pine) and from resins and balms (galbanum, elemi, benjoin, myrrh, olibanum, opopanax).

Examples of fragrancing substances are especially: limonene, geraniol, geranyl acetate, farnesol, borneol, bornyl acetate, linolool, linalyl acetate, linalyl propionate, linalyl butyrate, tetrahydrolinolool, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl) propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-4-heptylcyclopentanone, 3-methyl-2-pentyl-2-cyclopentenone, menthone, carvone, tagetone, geranylacetone, n-decanal, n-dodecanal, 9-decen-1-ol, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepinonitrile, hawthorn, heliotropin, coumarin, eugenol, vanillin, diphenyl ether, citral, citronellal, hydroxycitronellal, damascone, ionones, methylionones, isomethylionones, solanone, irones, cis-3-hexenol and esters thereof, muskindans, musk-tetralins, musk-isochromans, macrocyclic ketones, musk-macrolactones, aliphatic musks, ethylene brassylate and rose essence, and mixtures thereof.

b) Cosmetic Active Agents

The term "cosmetic active agent" means any molecule which has a hygiene, care, makeup or colouring effect contributing towards the improvement, well-being and/or enhancement or modification of the appearance of the human keratin material onto which the said composition is applied.

The cosmetic active agents may thus be chosen from any substance that satisfies this definition and that is present in the products, such as (i) hygiene products: makeup removers, toothpastes, deodorants, antiperspirants, shower gels, bath preparations (bubble baths, bath oils or bath salts), personal cleansing gels, soaps, shampoos, (ii) care products: antiwrinkle cream, day cream, night cream, moisturizing cream, floral water, scrubbing product, milk, beauty mask, lip balm, tonic, (iii) hair care and/or hair treatment products such as styling products, dye products, permanent-waving products, hair-conditioning products: hair conditioners, relaxer, straightener; gel, oil, lacquer, mask, antidandruff agents, (iv) makeup products: concealer, eyeliner, blusher, foundation, kohl, mascara, powder, skin-whitening product, lipstick, nail varnish, (v) fragrances: eau de Cologne, eau de toilette, perfume, (vi) antisun products: self-tanning products, after-sun creams, milks, oils, sticks or lotions and antisun products, (vii) shaving products and hair-removing products: aftershave, hair-removing creams, shaving foams and gels.

Among the active agents for caring for human keratin materials such as the skin, the lips, the scalp, the hair, the eyelashes or the nails, examples that may be mentioned include:

vitamins and derivatives or precursors thereof, alone or as mixtures;
antioxidants;
cleansing agents;
hair dyes;
conditioning agents;
agents for relaxing and/or straightening and/or shaping the hair;
free-radical scavengers;
antipollution agents;
photoprotective agents such as organic screening agents and mineral UV-screening agents;
self-tanning agents;
antiglycation agents;

calmatives;
hair-removing agents;
deodorants;
antiperspirants;
essential oils;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
dermo-relaxing agents,
refreshing agents;
tensioning agents;
matting agents;
depigmenting agents;
pro-pigmenting agents;
keratolytic agents;
desquamating agents;
moisturizers;
antimicrobial agents;
slimming agents;
agents that act on the energy metabolism of cells;
insect repellents;
substance P or CRGP antagonists;
hair-loss counteractants;
antiwrinkle agents;
antiageing agents;
antidandruff agents.

c) Pharmaceutical Active Principles

The term "pharmaceutical active principle" means a molecule which has a curative and/or prophylactic therapeutic effect.

For example, it may be any molecule with therapeutic properties that is included in the composition of a medicament. Examples that may be mentioned include non-steroidal anti-inflammatory drugs (NSAIDS), abortives, alpha-blockers, alpha2 agonists, aminosides, analgesics, anaesthetics, local anaesthetics, anorexigenics, 5HT3 antagonists, calcium antagonists, antiangina agents, antiarrhythmics, antibiotics, anticholinergics, anticholinesterases, antidiabetics, antidiarrhoeics, antidepressants, antihistamines, antihypertensives, antimycotics, antimalarials, antiparasitics, antipsychotics, antipyretics, antiretrovirals, antiseptics, antispasmolytics, antivirals, antiemetics, antiepileptics, anxiolytics, barbiturates, benzodiazepines, bronchodilators, beta-blockers, chemotherapeutic agents, corticosteroids, diuretics, loop diuretics, osmotic diuretics, depressants, glucocorticoids, hallucinogens, hypnotics, immunosuppressants, carbonic anhydrase inhibitors, neuraminidase inhibitors, proton pump inhibitors, TNF inhibitors, serotonin reuptake selective inhibitors, HMG-CoA reductase inhibitors (or statins), keratolytics, laxatives, mineralocorticoids, muscle relaxants, neuroleptics, psychotropics, spasmolytics, stimulants, sedatives, tocolytics or vasodilators. This list is not exhaustive and covers any therapeutic active principle known to those skilled in the art.

According to one embodiment of the invention, the encapsulated active agent may be impregnated onto solid particles, in particular inert solid particles.

The term "inert particles" means particles that do not chemically modify the encapsulated active agent.

The solid particles may be chosen from porous particles and hollow particles.

The solid particles may be chosen from silica, calcium carbonate, kaolin, talc, titanium dioxide, polyamide, (meth) acrylic polymer and glass particles.

The solid particles preferably have a mean size ranging from 10 nm to 50 µm and preferably ranging from 100 nm to 50 µm.

The term "porous particles" means particles with a structure comprising pores or interstices that are accessible to external agents. The structure of the particles may be of matrix type like a sponge.

Preferably, the porous particles have a specific surface area measured via the BET method ranging especially from 1 to 1000 $m^2/g$, in particular from 2 to 750 $m^2/g$, more particularly greater than or equal to 300 $m^2/g$ or even greater than or equal to 500 $m^2/g$. The BET (Brunauer-Emmet-Teller) method is a method that is well known to those skilled in the art, and is described especially in the *Journal of the American Chemical Society*, vol. 60, page 309, February 1938, and corresponds to international standard ISO 5794/1 (appendix D). The specific surface area measured according to the BET method corresponds to the total specific surface area, i.e. it includes the surface area formed by the pores.

The porous particles may be chosen from silica (micro) particles, crosslinked or non-crosslinked (meth)acrylic polymer particles, and polyamide particles, and mixtures thereof.

As organic porous particles that may be used, mention may be made of polyamide particles, in particular Nylon 6, Nylon 6-6, Nylon 12 or Nylon 6-12, such as those sold by the company Arkema under the name Orgasol.

Mention may also be made of acrylic polymer porous particles, such as polymethyl methacrylate (PMMA) particles, which are especially spherical, such as those sold under the name Covabead® by the company LCW.

Mention may also be made of crosslinked acrylic polymer porous particles, such as those having the INCI name: Acrylates/ethylhexyl acrylate crosspolymer, and in particular those sold under the name Techpolymer ACP 8-G by the company Sekisui Plastics; or alternatively particles of a copolymer of ethylene glycol dimethacrylate and of methyl methacrylate and also particles of polyallyl methacrylate and of ethylene glycol dimethacrylate.

As porous mineral particles, mention may be made of silica particles, which are especially spherical, sold under the name Silica Beads SB-700 by the company Miyoshi or Sunsphere® H51 and Sunsphere® H33 by the company Asahi Glass.

The hollow particles may be chosen from glass particles; polymer particles, especially of crosslinked or non-crosslinked, optionally thermoplastic, optionally expanded vinyl or (meth)acrylic polymer; and mixtures thereof.

As glass particles that may be used, mention may be made of hollow glass particles and especially those sold by the company 3M under the reference Scotchlite Glass Bubbles S 22.

As hollow polymer particles, especially of crosslinked or non-crosslinked vinyl, preferably acrylic, polymer, mention may be made in particular of crosslinked polymethyl methacrylate particles, and especially those sold by the company Sunjin Chemical under the name SUNPMMA H.

The hollow particles may also be hollow particles of one or more expanded thermoplastic polymers. They may be advantageously chosen from hollow particles of expanded thermoplastic copolymers of acrylonitrile, of vinylidene chloride, of vinyl chloride and/or of (meth)acrylic or styrene monomer. The (meth)acrylic monomer is, for example, a $C_1$-$C_4$ alkyl acrylate or methacrylate, especially methyl or ethyl acrylate or methacrylate. The styrene monomer is, for example, α-methylstyrene or styrene. Preferably, the particles according to the invention are particles of an expanded thermoplastic copolymer of vinylidene chloride and acrylonitrile or of vinylidene chloride, acrylonitrile and a $C_1$-$C_4$ alkyl(meth)acrylate, or of styrene monomer. Preferentially, the expanded polymer particles according to the invention are particles of an expanded copolymer of vinylidene chloride, acrylonitrile and a $C_1$-$C_4$ alkyl(meth)acrylate, especially of methyl or ethyl(meth)acrylate, and better still of methyl methacrylate.

It is possible, for example, to use a polymer containing 0-60% of units derived from vinylidene chloride, 20-90% of units derived from acrylonitrile and 0-50% of units derived from a $C_1$-$C_4$ alkyl(meth)acrylate or styrene monomer, the sum of the percentages (by weight) being equal to 100%.

It is most particularly possible to use a polymer containing 0-60% of units derived from vinylidene chloride, 20-90% of units derived from acrylonitrile and 0-50% of units derived from a $C_1$-$C_4$ alkyl(meth)acrylate monomer; especially from methyl or ethyl(meth)acrylate and better still from methyl methacrylate; the sum of the percentages (by weight) being equal to 100%.

Preferentially, the particles are hollow particles of an expanded polymer of vinylidene chloride and acrylonitrile or of vinylidene chloride, acrylonitrile and methyl methacrylate; preferably with a mean particle size of from 1 to 300 µm, for example from 5 to 200 µm, preferably from 10 to 100 µm and better still from 15 to 40 µm; preferably, the particles being hollow and optionally filled with a gas, chosen especially from air, nitrogen, isobutane and isopentane, preferentially isobutane.

Preferentially, the mass per unit volume of these particles is chosen in the range from 15 to 200 kg/m$^3$, better still from 40 to 120 kg/m$^3$ and even better still from 60 to 80 kg/m$^3$.

The particles that may be used in the context of the invention may be microspheres of an expanded terpolymer of vinylidene chloride, acrylonitrile and methyl methacrylate, such as those sold under the brand name Expancel by the company Nobel Casco and in particular under the references 551 DE 12 (particle size D(0.5) of about 12 µm and mass per unit volume of about 40 kg/m$^3$), 551 DE 20 (particle size D(0.5) of about 15 to 25 µm and mass per unit volume of about 60 kg/m$^3$), 551 DE 50 (particle size D(0.5) of about 40 µm), 461 DE 50 and 642 WE 50 of about 50 µm of particle size D(0.5) and 551 DE 80 (particle size D(0.5) of about 50 to 80 µm). It is also possible to use particles of this same expanded terpolymer with a particle size D(0.5) of about 18 µm and a mass per unit volume of about 60 to 80 kg/m$^3$ (Expancel EL23) or with a particle size D(0.5) of about 34 µm and a mass per unit volume of about 20 kg/m$^3$. Mention may also be made of the Expancel particles 551 DE 40 d42 (particle size D(0.5) of approximately 30 to 50 µm and mass per unit volume of approximately 42 kg/m$^3$), 551 DE 80 d42 (particle size D(0.5) of approximately 50 to 80 µm and mass per unit volume of approximately 42 kg/m$^3$), 461 DE 20 d70 (particle size D(0.5) of approximately 15 to 25 µm and mass per unit volume of approximately 70 kg/m$^3$), 461 DE 40 d25 (particle size D(0.5) of approximately 35 to 55 µm and mass per unit volume of approximately 25 kg/m$^3$), 461 DE 40 d60 (particle size D(0.5) of approximately 20 to 40 µm and mass per unit volume of approximately 60 kg/m$^3$), 461 DET 40 d25 (particle size D(0.5) of approximately 35 to 55 µm and mass per unit volume of approximately 25 kg/m$^3$), 051 DE 40 d60 (particle size D(0.5) of approximately 20 to 40 µm and mass per unit volume of approximately 60 kg/m$^3$), 091 DE 40 d30 (particle size D(0.5) of approximately 35 to 55 µm and mass per unit volume of approximately 30 kg/m$^3$) or 091 DE 80 d30 (particle size D(0.5) of approximately 60 to 90 µm and mass per unit volume of approximately 30 kg/m$^3$).

Preferably, the composition according to the invention comprises hollow particles, alone or as a mixture with porous particles.

In a preferred embodiment, the composition comprises hollow particles of one or more expanded thermoplastic polymers.

The capsules according to the invention may be prepared via several processes, especially depending on the nature of the active agent to be encapsulated.

Process 1

According to a first method for preparing the capsules according to the invention, when the active agent is liquid at room temperature (25° C.) and insoluble in water at 25° C. (solubility of less than 0.1% by weight) or when the solid active agent is insoluble in water and dissolved in an organic solvent, an oil-in-water emulsion is prepared by emulsifying the active agent, optionally dissolved in an organic solvent, in water in the presence of an oil-in-water emulsifying surfactant. Such a surfactant is especially chosen, in a known manner, from surfactants with an HLB (hydrophilic-lipophilic balance) value of between 8 and 18.

The emulsification may be performed at a temperature of between 0 and 100° C. especially, and for 1 to 60 minutes, with suitable mechanical stirring or with ultrasonication.

Next, the cationic polymer (second polymer) is added to the emulsion, especially in the form of a saline aqueous solution (sodium chloride content of between 0.01 M and 3 M). The emulsion is advantageously stirred, especially for 1 to 30 minutes.

The reaction mixture is advantageously centrifuged with a power of between 1000 and 10 000 rpm and the supernatant discarded. Next, the first polymer (polymer bearing a photosensitive group) is added, especially in the form of a saline aqueous solution (sodium chloride concentration of between 0.01 M and 3 M). The mixture is advantageously stirred or subjected to ultrasonication for 1 to 10 minutes. Advantageously, the reaction mixture is centrifuged and the supernatant discarded.

Several cycles of addition of the second cationic polymer and of the first polymer (amino polymer bearing a photosensitive group) may be performed up to the desired number of layers of these polymers (for example from 1 to 10 times).

At the end of the addition of the first and second polymers and removal of the final supernatant, the capsules obtained are advantageously washed with water and the mixture is then centrifuged. The capsules are recovered after removal of the supernatant.

Process 2

According to a second method for preparing the capsules according to the invention, the active agent to be encapsulated is first impregnated onto solid particles as described previously and the impregnated solid particles are then successively coated with the first and second polymers.

According to this process, if the active agent is in solid form, it is first mixed (dissolved) with a protic or aprotic solvent and the solid particles are then added to the mixture. If the active agent is liquid at room temperature, it may be used alone without using a solvent. Advantageously, the mixture is left, with or without stirring, for a time ranging from 10 minutes to 24 hours to allow the diffusion of the active agent into the solid particles. Advantageously, the solid particles impregnated with active agent are isolated by filtration or by centrifugation.

Next, the second polymer (cationic polymer) is added to the impregnated solid particles, especially in the form of a saline aqueous solution (sodium chloride concentration of between 0.01 M and 3 M) and the mixture is advantageously left for 1 to 30 minutes. Advantageously, the reaction mixture is centrifuged with a power of between 1000 and 10 000 rpm and the supernatant discarded. Next, the first polymer is added to the impregnated solid particles, especially in the form of a saline aqueous solution (sodium chloride concentration of between 0.01 M and 3 M). Advantageously, the mixture is stirred or subjected to ultrasonication for 1 to 10 minutes. Advantageously, the reaction mixture is centrifuged and the supernatant discarded.

Several cycles of addition of the second cationic polymer and of the first polymer (amino polymer bearing a photosensitive group) may be performed up to the desired number of layers of these polymers (for example from 1 to 10 times).

When the solid particles are calcium carbonate particles, a post-treatment of the capsules obtained may be performed with an aqueous solution of ethylenediaminetetraacetic acid or an aqueous 0.5 N solution of hydrochloric acid, especially for 2 hours to 24 hours, at room temperature. This treatment makes it possible to dissolve the calcium carbonate while at the same time leaving the active agent coated with the first and second polymers.

Process 3

According to a third method for preparing the capsules according to the invention, solid particles are formed in the presence of the active agent and coating of the impregnated solid particles with the first and second polymers is then performed.

An example of such a process is the preparation of solid calcium carbonate particles in the presence of active agent. An aqueous calcium chloride or nitrate solution and the active agent are mixed together and stirred for 5 minutes. Next, an equimolar solution (equimolar to the calcium chloride or nitrate solution) of sodium or ammonium carbonate is added, especially over 5 minutes. Advantageously, the reaction mixture is stirred for 10 minutes to 24 hours. Next, the reaction mixture is advantageously centrifuged with a power of between 1000 and 10 000 rpm and the supernatant discarded. Precipitation allows the particles to be recovered. Next, the second polymer is added to the solid particles, especially in the form of a saline aqueous solution (sodium chloride concentration of between 0.01 M and 3 M). Advantageously, the mixture is stirred or subjected to ultrasonication for 1 to 10 minutes. Advantageously, the reaction mixture is centrifuged and the supernatant discarded.

Several cycles of addition of the second cationic polymer and of the first polymer (amino polymer bearing a photosensitive group) may be performed up to the desired number of layers of these polymers (for example from 1 to 10 times).

At the end of the addition of the first and second polymers and removal of the final supernatant, the capsules obtained are advantageously washed with water and the mixture is then centrifuged. The capsules are recovered after removal of the supernatant.

The preparation of the solid particles described previously may be performed in the presence of a polysaccharide polymer. This polysaccharide aids the formation of the solid particles and the impregnation of the active agent into these formed particles.

The polysaccharide may be chosen from starch, cellulose, guar gum, gum arabic (INCI name: acacia senegal gum), alginic acid, alginate salts (especially sodium, calcium and zinc salts) and carrageenans. Preferably, the polysaccharide is chosen from alginate salts. Preferentially, the polysaccharide is sodium alginate.

In the first preparation method described previously, the emulsifying surfactant used may be chosen from:

The Following Nonionic Surfactants:

esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives comprising oxyethylene and/or oxypropylene units which may comprise from 1 to 150 oxyethylene and/or oxypropylene units and preferably from 20 to 100 oxyethylene units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; fatty alcohol ethers of $C_8$-$C_{24}$ fatty acids, and the oxyalkylenated derivatives thereof; the sugar ethers of $C_8$-$C_{24}$ fatty alcohols, and mixtures thereof.

Mention may in particular be made, as glyceryl ester of fatty acid, of glyceryl stearate (glyceryl mono-, di- and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol mono-, di- and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Examples of fatty alcohol ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Mention may be made, for example, of ethers comprising from 1 to 200 and preferably from 2 to 100 oxyethylene groups, such as those with the CTFA name Ceteareth-20 or Ceteareth-30, and mixtures thereof.

Examples of sugar mono- or polyalkyl esters or ethers that may be mentioned include the methylglucose isostearate sold under the name Isolan-IS by the company Degussa Goldschmidt, or else the sucrose distearate sold under the name Crodesta F50 by the company Croda, and the sucrose stearate sold under the name Ryoto sugar ester S 1570 by the company Mitsubishi Kagaku Foods.

Mention may also be made of lipoamino acids and salts thereof, such as monosodium and disodium acylglutamates, for instance monosodium stearoyl glutamate, sold under the name Amisoft HS-11PF, and disodium stearoyl glutamate, sold under the name Amisoft HS-21P, by Ajinomoto.

The Following Anionic Surfactants:

alkyl phosphates; alkyl sulfates, and in particular alkyl ether sulfates, alkylamido ether sulfates, alkylaryl polyether sulfates and monoglyceride sulfates;

alkyl sulfonates, alkylamide sulfonates, alkylaryl sulfonates, α-olefin sulfonates, paraffin sulfonates; alkylsulfosuccinates, alkyl ether sulfosuccinates, alkylamide sulfosuccinates; alkyl sulfosuccinamates; alkylsulfoacetates; acylsarcosinates, acylglutamates, acylisethionates, N-acyltaurates, acyllactylates; alkylpolyglycoside carboxylic esters such as alkylglucoside citrates, alkylpolyglycoside tartrates and alkylpolyglycoside sulfosuccinates, alkylpolyglycoside sulfosuccinamates; fatty acids, in particular the salts of oleic, ricinoleic, palmitic or stearic acid, and coconut oil or hydrogenated coconut oil acids; alkyl D-galactoside uronic acids and salts thereof, polyoxyalkylenated alkyl ($C_6$-$C_{24}$) ether carboxylic acids, polyoxyalkylenated alkyl($C_6$-$C_{24}$)aryl ether carboxylic acids, polyoxyalkylenated alkyl($C_6$-$C_{24}$) amido ether carboxylic acids and salts thereof, in particular those comprising from 2 to 50 alkylene oxide groups, in particular ethylene oxide groups;

The term "alkyl" means a $C_8$-$C_{24}$, better still $C_{12}$-$C_{20}$ and more preferentially $C_{14}$-$C_{18}$ alkyl group.

The term "acyl" means a $C_8$-$C_{24}$, better still $C_{12}$-$C_{20}$ and more preferentially $C_{14}$-$C_{18}$ acyl group.

Thus, the core of the capsule may therefore comprise, in addition to the active agent, an oil-in-water emulsifying surfactant such as those described previously, especially when the active agent is liquid at room temperature (25° C.) (the active agent flows under its own weight in less than 10 minutes) and insoluble in water at 25° C. (solubility of less than 0.1% by weight), or when the active agent is solid at room temperature, insoluble in water and soluble in a water-immiscible organic solvent (miscibility of less than 0.1% by weight) (all the conditions being at room temperature, 25° C.). In this case, the polymer layer of the shell of the capsule in contact with the active agent (i.e. the first layer) is advantageously the cationic polymer (second polymer).

The surfactant and the encapsulated active agent may be present in the capsules in contents such that the surfactant/active agent weight ratio ranges from 0.1 to 10.

The core of the capsule may also comprise one or more solid particles as described previously, and optionally a solvent to dissolve the encapsulated active agent when the active agent is a solid (at room temperature).

The solid particles and the encapsulated active agent may be present in the capsules in contents such that the active agent/solid particles weight ratio ranges from 0.001 to 10.

The first and second polymers described previously may be present in the capsules in a first polymer/second polymer weight ratio ranging from 0.5 to 1.5, preferably ranging from 0.6 to 1.4, preferentially ranging from 0.7 to 1.3, more preferentially ranging from 0.8 to 1.2 and better still ranging from 0.9 to 1.1.

Advantageously, the encapsulated active agent may be present in a content such that the (first polymer+second polymer)/active agent weight ratio ranges from 0.005 to 40, preferably from 0.05 to 20 and preferentially from 0.05 to 5.

The capsules according to the invention may have a mean size ranging from 80 nm to 80 microns and preferably ranging from 200 nm to 30 microns.

The invention also relates to a cosmetic composition comprising, in a physiologically acceptable medium, capsules as described previously containing an active agent chosen from fragrancing substances and cosmetic active agents.

The invention also relates to a pharmaceutical composition comprising, in a physiologically acceptable medium, capsules as described previously containing an active agent chosen from pharmaceutical active agents.

The capsules according to the invention may be present in the cosmetic or pharmaceutical composition in a content ranging from 0.1% to 50% by weight, relative to the total weight of the composition, preferably ranging from 0.5% to 40% by weight, preferentially ranging from 1% to 30% by weight.

In a known manner, the cosmetic or pharmaceutical composition of the invention may also contain adjuvants that are common in cosmetics or pharmaceuticals, such as water, organic solvents, oils, waxes, antioxidants, fragrances, essential oils, preserving agents, cosmetic active agents, moisturizers, vitamins, ceramides, sunscreens, surfactants, thickeners, dispersants, antifoams, neutralizers and polymers, and mixtures thereof.

The amounts of these various adjuvants are those conventionally used in the field under consideration.

The cosmetic composition may be a composition for caring for the skin, for cleansing the skin or the hair (shampoo), a haircare composition, a makeup composition, an antisun composition or a body hygiene composition (deodorant or antiperspirant). Advantageously, the cosmetic composition is a leave-on composition.

The non-therapeutic cosmetic process according to the invention comprises a step of applying to the keratin materials the cosmetic composition comprising the capsules, followed by a step that consists in exposing the capsules deposited on the keratin materials to a light radiation with a wavelength of between 360 and 600 nm.

Preferably, the light radiation used in the process according to the invention has a wavelength of between 400 and 450 nm.

The light radiation preferably has a flux (amount of energy per unit surface area) ranging from 3 to 100 $J/cm^2$ and preferably ranging from 3 to 10 $J/cm^2$.

The light radiation may be natural light.

The light radiation may be continuous or non-continuous light.

Sources of light radiation that may be mentioned include arc lamps such as xenon lamps and mercury lamps; fluorescent lamps; incandescent lamps such as halogens; LEDs and lasers. Filters, for screening out radiation with wavelengths of less than 360 nm or greater than 450 nm, may be used with these lamps.

Mention may be made especially of goLITE BLU from the company Philips, the lamp Energylight HF 3319/01 from the company Philips, the lamps Dayvia White and Messa from the company Solvital, the lamp Lumino Plus from the company Lanaform, the lamp Medibeam from the company Medibeam, the lamp M-LED 01 from the company Meimed, the lamp Lifemax Light Pod from the company Lifemax, the lamp Lite-Pad from the company Reicorp, and the lamp Camag Box 3 (4×8 W) from the company Camag.

The time of exposure to the light radiation of the capsules deposited on the keratin materials may range from 1 microsecond to 1 hour or from 1 minute to 1 hour. The light exposure time may be repeated several times, especially to allow a release of the encapsulated active agent over a long period.

The keratin fibre treatment process may be applied to the skin, the hair, the nails, the eyelashes or the lips. It may be a process for caring for or fragrancing keratin materials.

The invention is illustrated in greater detail by the examples described below.

EXAMPLE 1

0.1 g of limonene and 0.4 g of aqueous sodium dodecyl sulfate solution (20 mM) were placed in a glass flask. The mixture was ultrasonicated at 20 kHz for 2 minutes. Next, 1 ml of aqueous polydiallyldimethylammonium chloride solution (2 mg/ml in 0.5 M NaCl) 200-350 kDa from the company Sigma (ref. 409022) were added and the mixture was ultrasonicated at 20 kHz for 2 minutes. The mixture was centrifuged at 6000 rpm for 3 minutes. The supernatant was discarded. Next, 1 ml of aqueous poly{1-[4-(3-carboxy-4-hydroxyphenylazo)benzenesulfonamido]-1,2-ethanediyl, sodium salt} (PAZO from the company Sigma, ref. 346411; degree of substitution>90%) (2 mg/ml in 0.5 M NaCl) was added. After 15 minutes, the mixture was centrifuged at 6000 rpm for 3 minutes. The supernatant was discarded. Next, the following cycle was repeated five times: addition of 1 ml of aqueous polydiallyldimethylammonium chloride solution (2 mg/ml in 0.5 M NaCl); after 15 minutes, centrifugation of the mixture at 6000 rpm for 3 minutes; removal of the supernatant; washing of the remaining gel with 3 ml of water and then centrifugation at 6000 rpm for 3 minutes.

The final emulsion obtained comprises limonene capsules with a number-average size of 1338 nm (measured by light scattering with a Zetasizer® machine from the company Malvern Instruments).

COMPARATIVE EXAMPLE 1'

Capsules were prepared according to the procedure of Example 1, but replacing the PAZO polymer with poly(4-styrene sulfonate) $M_W$ 70 kDa (reference 243051 from Sigma-Aldrich).

The final emulsion obtained comprises limonene capsules with a number-average size of 2660 nm.

EXAMPLE 2

2 ml of limonene and 0.11 g of calcium carbonate particles were placed in a glass flask for 2 hours. The mixture was centrifuged (1500 rpm for 1 minute) and the solid particles were then recovered.

Next, 1 g of aqueous polydiallyldimethylammonium chloride solution (PDADMAC) (2 mg/ml in 0.5 M NaCl) 200-350 kDa from the company Sigma (ref. 409022) were added and the mixture was left to stand for 10 minutes. The mixture was centrifuged at 1500 rpm for 1 minute. The supernatant was discarded. Next, 1 ml of aqueous poly{1-[4-(3-carboxy-4-hydroxyphenylazo)benzenesulfonamido]-1,2-ethanediyl, sodium salt} (PAZO from the company Sigma, ref. 346411) (2 mg/ml in 0.5 M NaCl) was added. After 10 minutes, the mixture was centrifuged at 1500 rpm for 1 minute. The supernatant was discarded. The remaining gel was washed with 1 ml of water and then centrifuged (1500 rpm for 1 minute). Next, the following cycle was repeated five times: addition of 1 ml of aqueous PDADMAC solution (2 mg/ml in 0.5 M NaCl); after 10 minutes, centrifugation of the mixture at 1500 rpm for 1 minute; removal of the supernatant; washing of the remaining gel with 1 ml of water and then centrifugation at 1500 rpm for 1 minute.

After the final wash, the capsules obtained were suspended in 2 ml of distilled water and stored protected from light. The capsules obtained have a mean particle size of 5.45 μm (measured by optical microscopy with a MorphologiG3® machine from the company Malvern Instruments).

COMPARATIVE EXAMPLE 2'

Capsules were prepared according to the procedure of Example 1, but replacing the PAZO polymer with poly(4-styrene sulfonate) $M_W$ 70 kDa (reference 243051 from Sigma-Aldrich).

The capsules obtained have a mean particle size of 5.56 μm.

EXAMPLE 3

An aqueous calcium chloride solution (615 μl, 1 M) was added to an aqueous adenosine solution (1.34 ml, 0.45 M) and then stirred for 5 minutes. A sodium carbonate solution (615 μl, 1 M) was added over 5 minutes (dropwise). The reaction mixture was stirred for 1 hour. Next, the reaction mixture was centrifuged (1500 rpm, 1 minute) and the supernatant discarded. 2 ml of a PDADMAC solution (2 mg/ml in 0.5 M NaCl) were added to the particles. The mixture was stirred for 10 minutes and then centrifuged, and the supernatant discarded. 2 ml of a PAZO solution (2 mg/ml in 0.5 M NaCl) were added to the particles. The mixture was stirred for 10 minutes and then centrifuged (1500 rpm, 1 minute) and the supernatant discarded. The following cycle was then repeated five times: addition of PDADMAC and then of PAZO. At the end of addition of the polymers and removal of the final supernatant, the capsules formed were washed with 5 ml of water and the mixture was then centrifuged. The capsules obtained have a number-average diameter of 7.5 microns.

COMPARATIVE EXAMPLE 3'

Capsules were prepared according to the procedure of Example 3, but replacing the PAZO polymer with poly(4-styrene sulfonate) $M_W$ 70 kDa (reference 243051 from Sigma-Aldrich).

EXAMPLE 4

An aqueous calcium chloride solution (824 μl, 1 M) was added to an aqueous solution of adenosine (3 ml, 0.45 M) and of sodium alginate (3 ml, 1 mg/ml) and then stirred for 5 minutes. A sodium carbonate solution (824 μl, 1 M) was added over 5 minutes. The reaction mixture was stirred for 1 hour. Next, the reaction mixture was centrifuged (1500 rpm, 1 minute) and the supernatant discarded. 2 ml of a PDADMAC solution (2 mg/ml in 0.5 M NaCl) were added to the particles. The mixture was stirred for 10 minutes and then centrifuged, and the supernatant discarded. 2 ml of a PAZO solution (2 mg/ml in 0.5 M NaCl) were added to the particles. The mixture was stirred for 10 minutes and then centrifuged (1500 rpm) and the supernatant discarded. The following cycle was then repeated five times: addition of PDADMAC and then of PAZO. At the end of addition of the polymers and removal of the final supernatant, the capsules were washed with 5 ml of water and the mixture was then centrifuged. The capsules obtained have a number-average diameter of 9.1 microns.

EXAMPLE 5

Capsules were prepared according to the procedure of Example 3, but replacing the calcium chloride with calcium nitrate.

The capsules obtained have a mean particle size of 8.2 μm.

COMPARATIVE EXAMPLES 6 to 9

The following four lotions were prepared:

| Example | 0.3 g of fragranced capsules | Water |
|---|---|---|
| 6 (invention) | Example 1 | 10 ml |
| 7 (outside the invention) | Example 1' | 10 ml |
| 8 (invention) | Example 2 | 10 ml |
| 9 (outside the invention) | Example 2' | 10 ml |

Locks of blonde hair (2 g of hair) were soaked in 30 ml of tap water for 30 seconds and the excess water was then absorbed on absorbent paper. Each lotion (shaken beforehand) was applied (amount of 0.5 g) to 2 locks. The treated locks were or were not then irradiated, and the release of the encapsulated fragrance applied to the hair was assessed sensorily.

Figure 1:
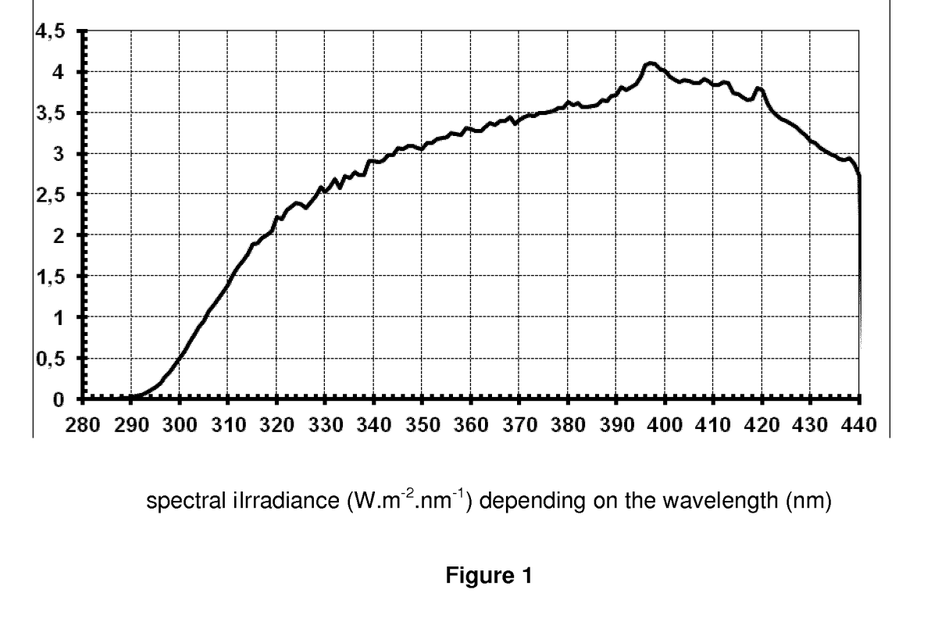
FIG. 1 is a graph of the spectral irradiance depending on wavelength.

The irradiation consisted in exposing the locks to light generated by a sunlight simulator (Oriel LOT 1000 W with the irradiation characteristics given in FIG. 1), with a distance of 25 cm between each lock and the light outlet.

Several irradiation times were applied to the locks, followed by sensory evaluation of the treated lock:
for 1 hour
for 8 hours
for 3 days consisting, in point of fact, of 8 hours of irradiation, then 16 hours without irradiation, then 8 hours of irradiation, then 16 hours without irradiation and then 8 hours of irradiation.

Immediately after the irradiation times, a sensory estimation test was performed. The locks were held 10 cm from the nose for 3 seconds and the person attributed a grade of evaluation of the perfume smelled from 0 to 5.

0 represents no perfume odour and 5 represents a strong perfume odour (equal to the odour of a bottle of pure limonene).

The following results were obtained:

| Lock number | Lotion applied | Irradiated |
|---|---|---|
| 1 | 3 | Yes |
| 2 | 3 | No |
| 3 | 4 | Yes |
| 4 | 4 | No |
| 5 | 5 | Yes |
| 6 | 5 | No |
| 7 | 6 | Yes |
| 8 | 6 | No |

| | Assessment grade (0 to 5) | | | |
|---|---|---|---|---|
| Lock number | 0 h | 1 h | 8 h | 3 d |
| 1 (invention) | 1 | 4 | 4 | 3 |
| 2 | 1 | 1 | 2 | 1 |
| 3 | 1 | 2 | 1 | 0 |
| 4 | 1 | 2 | 2 | 0 |
| 5 (invention) | 1 | 4 | 4 | 3 |
| 6 | 1 | 2 | 2 | 0 |
| 7 | 1 | 1 | 1 | 1 |
| 8 | | 2 | 2 | 1 |

It was found that the locks of hair treated with the lotions containing the fragrance capsules in accordance with the invention (locks 1 and 5) have a stronger fragrance intensity after 1 hour, 8 hours and 3 days than the locks treated with the lotions containing the capsules according to the invention and not irradiated (locks 2 and 6).

the locks treated with the lotions containing the non-photostimulable capsules (Examples 1' and 2') and irradiated (locks 3 and 7)

the locks treated with the lotions containing the non-photostimulable capsules (Examples 1' and 2') and not irradiated (locks 4 and 8).

COMPARATIVE EXAMPLES 10 and 11

The release of adenosine was studied for the capsules of Examples 3 and 3' exposed to light, in artificial sweat.

100 g of artificial sweat were manufactured by placing 0.5 g of sodium chloride, 0.1 g of lactic acid and 0.1 g of urea in a 200 ml beaker. The pH of the solution was then adjusted to 5.5 with ammonium hydroxide. 99.2 g of distilled water were then added.

15.6 mg of adenosine microcapsules of Example 3 were dispersed in 6 ml of artificial sweat.

Figure 2:
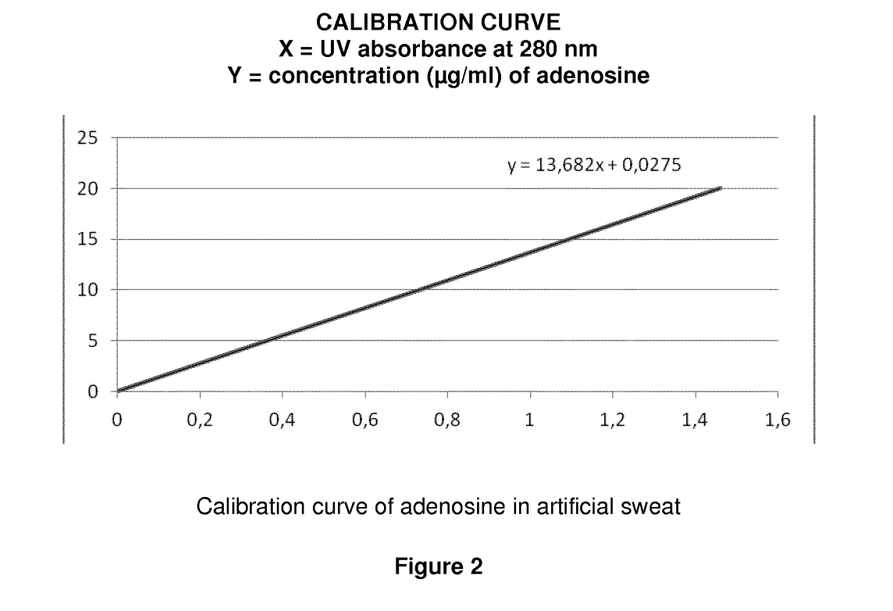
FIG. 2 is a calibration curve of adenosine in artificial sweat.

The solution was stirred with a magnetic stirrer and irradiated with a sunlight simulator (Oriel LOT 1000 W with the irradiation characteristics given in FIG. 1) for 4 hours. The solution was then centrifuged at 1500 rpm for 2 minutes. The supernatant was recovered and its UV-visible spectrum was recorded. Using the absorbance information from the UV-visible spectrum, the amount of adenosine released was calculated by means of the equation of the calibration curve indicated in FIG. 2.

The experiment was also performed with the adenosine capsules of Example 3' (outside the invention).

Similar but unirradiated lotions were also compared.

The following results were obtained:

| Example | Irradiated | UV absorbance at 280 nm | Concentration of adenosine released (µg/ml) |
|---|---|---|---|
| Capsules of Example 3 | Yes | 0.94 | 12.88 |
| Capsules of Example 3 | No | 0 | 0 |
| Capsules of Example 3' | Yes | 0.12 | 1.66 |
| Capsules of Example 3' | No | 0.17 | 2.35 |

It was found that the particles of Example 3 release adenosine only when they have been exposed to light; without irradiation the capsules are leaktight.

The particles of Example 3' release very little adenosine after exposure to light; and without irradiation, the capsules are not leaktight.

EXAMPLE 12

Depigmenting Lotion

A skin depigmenting composition comprising the ingredients below is prepared:

| | |
|---|---|
| Crosslinked acrylic acid (Carbopol 941) | 0.3 g |
| Capsules of Example 3 | 10 g |
| Preserving agents | qs |
| Water qsp | 100.0 g |

The composition is applied to the skin and the treated skin is then exposed to daylight for 15 minutes to release the adenosine from the capsules.

The capsules of Example 3 may be replaced with those of Example 4 or 5.

The invention claimed is:

1. Capsules of core/shell type, the core comprising an active agent; comprising one or more concentric and alternating layers of a first photosensitive anionic polymer and of a second cationic polymer, wherein the first photosensitive anionic polymer is selected from the group of a substituted polyallylamine bearing primary amine groups substituted at a degree of substitution of at least 50% (numerical degree), with a group of formula (Ia) below:

in which:

R and R' denote, independently, a hydrogen atom or a $C_1$-$C_4$ alkyl group or a $C_1$-$C_4$ alkoxy group, or a chlorine or fluorine atom or a nitro group;

R and R' may together form a $C_6$ aromatic ring;

Y denotes a —COOH or —SO$_3$H group;

R" and R'" being such that:

when Y=—COOH, R"=R'"=H or R"=—OCH$_3$ and R"=H or R"=OH and R'"=H or R"=Cl and R'"=H or R"=—CH$_3$ and R'"=H or R"=OCH$_3$ and R'"=OCH$_3$ or R"=—NCO—CH$_3$ and R'"=H or R"=isopropyl and R'"=CH$_3$ or R"=H and R'"=F or R"=isopropyl and R'"=H;

when Y=—SO$_3$H, R"=R'"=H or R" and R'" together form a $C_6$ aromatic ring;

or salts thereof; and poly{1-[4-(3-carboxy-4-hydroxyphenylazo)benzenesulfonamido]-1,2-ethanediyl or salts thereof;

and wherein the capsules are leaktight.

2. Capsules according to claim 1, wherein the substituted polyallylamine has a degree of substitution of greater than 60%.

3. Capsules according to claim 1, wherein the first polymer is poly{1-[4-(3-carboxy-4-hydroxyphenylazo)benzenesulfonamido]-1,2-ethanediyl, sodium salt}.

4. Capsules according to claim 1, wherein the second cationic polymer is chosen from dimethyldiallylammonium chloride homopolymers.

5. Capsules according to claim 1, wherein the first and second polymers are present in the capsules in a first polymer/second polymer weight ratio ranging from 0.5 to 1.5.

6. Capsules according to claim 1, wherein the weight ratio of the first polymer plus the second polymer to the active agent ranges from 0.005 to 40.

7. Capsules according to claim 1, wherein the core comprises an oil-in-water emulsifying surfactant when the active agent is liquid at room temperature and insoluble in water at 25° C. or when the active agent is solid at room temperature, insoluble in water and soluble in a water-immiscible organic solvent; all the conditions being at room temperature, 25° C.

8. Capsules according to claim 1, wherein the core comprises one or more solid particles impregnated with the encapsulated active agent, and optionally a solvent to dissolve the encapsulated active agent when the active agent is a solid at room temperature.

9. Capsules according to claim 8, wherein the particles are chosen from porous particles and hollow particles.

10. Capsules according to claim 8, wherein the solid particles are chosen from silica, calcium carbonate, kaolin, talc, titanium dioxide, polyamide, (meth)acrylic polymer and glass particles.

11. Capsules according to claim 8, wherein the solid particles have a mean size ranging from 10 nm to 50 μm.

12. Capsules according to claim 1, wherein the capsules have a mean size ranging from 80 nm to 80 microns.

13. Capsules according to claim 1, wherein the encapsulated active agent is chosen from fragrancing substances and cosmetic active agents.

14. Cosmetic composition comprising, in a physiologically acceptable medium, capsules according to claim 13.

15. Non-therapeutic cosmetic process for treating keratin materials, comprising the application to the keratin materials of a cosmetic composition according to claim 14, followed by exposure of the deposit formed on the keratin materials to natural light or to artificial light with a wavelength of between 360 and 600 nm.

16. Capsules according to claim 1, wherein the encapsulated active agent is chosen from pharmaceutical active principles.

17. Pharmaceutical composition comprising, in a physiologically acceptable medium, capsules according to claim 1, wherein the encapsulated active agent is chosen from pharmaceutical active principles.

18. Capsules according to claim 1, wherein the second cationic polymer is selected from the group of homopolymers and copolymers of dimethyldiallylammonium salts and mixtures thereof.

19. Capsules according to claim 1, wherein the first polymer is poly{1-[4-(3-carboxy-4-hydroxyphenylazo)benzenesulfonamido]-1,2-ethanediyl, sodium salt, the second cationic polymer is chosen from dimethyldiallylammonium chloride homopolymers, the first and second polymers are present in the capsules in a first polymer/second polymer weight ratio ranging from 0.5 to 1.5 and the encapsulated active agent is chosen from fragrancing substances.

* * * * *